United States Patent
Chuah et al.

(10) Patent No.: US 6,257,761 B1
(45) Date of Patent: Jul. 10, 2001

(54) INSULATION MEASURING APPARATUS WHICH FORCES HEAT FLOW IN ONE DIRECTION WITH A CONSTANT TEMPERATURE REGION

(75) Inventors: Yew Khoy Chuah, Taipei; Ming-Tsun Sun, Taoyuan; Bin-Juine Huang, Taipei, all of (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/000,785

(22) Filed: Dec. 30, 1997

(51) Int. Cl.[7] .......................... G01N 25/20; G01N 25/00; G01K 17/00; G01K 1/08
(52) U.S. Cl. ........................... 374/208; 374/45; 374/137; 374/166
(58) Field of Search .................................. 374/43, 44, 45, 374/30, 137, 166, 208

(56) References Cited

U.S. PATENT DOCUMENTS

| | | | |
|---|---|---|---|
| 4,155,244 | * | 5/1979 | Bhattacharyya ........................ 374/44 |
| 4,364,676 | * | 12/1982 | Oja et al. ................................. 374/44 |
| 4,381,154 | * | 4/1983 | Hammond ............................... 374/43 |
| 4,647,221 | * | 3/1987 | Szabo ..................................... 374/44 |
| 4,906,105 | * | 3/1990 | Geake ..................................... 374/30 |
| 5,667,301 | * | 9/1997 | Jurkowski et al. ..................... 374/43 |
| 5,702,185 | * | 12/1997 | Heikal ..................................... 374/43 |

OTHER PUBLICATIONS

1. Collins et al., "Transparent Evacuated Insulation," *Solar Energy*, vol. 49, No. 3, p. 333–350, 1992.
2. Collins et al., "Evacuated Glazing," *Solar Energy*, vol. 47, No. 1, p. 27–38, 1992.
3. "Quick Thermal Conductivity Meter", Catalog by Kyoto Electronics Manufacturing Co., Ltd. (Feb. 1990).
4. "Thermal Conductivity Meter", Catalog by Tokyo Electronic Industrial Co., Ltd. (1989).

* cited by examiner

Primary Examiner—Diego Gutierrez
Assistant Examiner—Jeanne-Marguerite Goodwin
(74) Attorney, Agent, or Firm—Birch, Stewart, Kolasch & Birch, LLP

(57) ABSTRACT

This invention makes use of a electronically controlled heating device to form a region of constant high temperature on one side of the insulating material, and causes most of the heat transfer to concentrate in a longitudinal heat flux, which flows across the direction of the thickness of object-to-be-tested, to achieve the effect of one-dimensional heat transfer. When the temperatures on both sides of the insulation material being tested come to a stable state, the temperatures, the thickness of the material, and the heat flux, are measured and used to calculate the heat conductivity. The difference between the ideal two-dimensional heat transfer and the one-dimensional heat transfer can be corrected by the results of a theoretical model. The apparatus has been used to test a material with known heat conductivity. The result of the test conforms well with the expected value. Currently, the prototype which has been developed may be designed with a digital circuit which consists mainly of a single-chip microcomputer to perform PWM (Pulse Width Modulation) temperature control, temperature measurement, parameter input and coefficient calculation and displays functions.

5 Claims, 9 Drawing Sheets

INSULATION MEASURING APPARATUS WHICH FORCES HEAT FLOW IN ONE DIRECTION WITH A CONSTANT TEMPERATURE REGION

BACKGROUND OF THE INVENTION

1. Field of the Invention

This invention disclosed an electronically controlled heating device, this used device to form a region of constant high temperature on one side of the insulating material, and causes most of the heat transfer to concentrate in a longitudinal heat flux, which flows across the direction of the thickness of object-to-be-tested, to achieve the effect of one-dimensional heat transfer.

2. Background of the Invention

Insulation technique may be applied with improved quality, manufacturing process, or structure of the insulating material. Whether it is the improvement in the quality of existing insulating material, or evaluating the on-site insulating proficiency as the basis of improvement, the testing of the insulating effectiveness remains a necessity.

In general, testing of insulating effectiveness is limited within the laboratory, and requires the use of test pieces for measurement. Direct application on the entire product is not possible. For testing of insulating effectiveness on compound materials, especially the testing of a vacuum insulating layer or an on-site insulating layer, it is even more impossible to cut off the insulating layer and make them into test pieces to be placed into a traditional heat-flow gauge/insulation measuring apparatus for testing.

Currently, an apparatus which may be used for measuring on-site heat insulation is Japan's QTM (Quick Testing Method). It estimates the k value from temperature changes on the surface of the insulating material but may only be used on objects which are thicker and are made of a homogeneous material. Therefore, it is primarily used on construction materials such as cement wall. Generally, testing of insulating materials is limited within the laboratory and requires the use of test pieces for measurement, and may not actually be conducted on the product itself.

A similar insulation measuring apparatus is reported by R. E. Collins, et al, in 1992 and published in *Transparent Evacuated Insulation* (*Solar Energy*), Volume 49, 3rd issue, pp. 333–350. It utilizes hot water (21) and cold water (22) to maintain constant temperatures on two sides. In the middle region above them, there is an electric temperature-control device (23) which is maintained at the same temperature with that of the upstream hot water (21), and the coefficient of the heat transfer point is calculated from the temperature difference between the top and the bottom, and the electro-calorific value. Its defects are: a) water which is used as a medium for heat control needs to be maintained at a certain temperature; Collins insulation measuring apparatus has a complex structure and enormous size; b) it can only test the test pieces and cannot test the actual object.

Problems Which the Invention Intends to Resolve

In view of past methods for evaluating insulating effectiveness of materials or on-site insulating effectiveness, this invention can utilize a non-destructive approach to measure the insulating effectiveness of frozen/air-conditioned products, and can be used for quality inspection of the insulating effectiveness of products.

This invention has been designed as a portable and stabilized prototype insulating effectiveness measuring apparatus, which has a portable feature, and is suitable for use in measuring the insulating effectiveness of frozen/air-conditioned products. Not only is it beneficial for random product inspection and research for energy conservation, it also compensates the defects of the Quick Testing Method.

One other critical feature of this invention is its utilization of the theory of zero heat transfer in a region with uniform temperature to cause heat to flow in a single direction, thus leading to the design of an electrically controlled heating device.

SUMMARY OF THE INVENTION

In this invention, an electrically controlled heating device is installed on one side of the insulating material, which causes most of the heat transfer to concentrate in a longitudinal heat flux, which flows across the direction of the thickness of object-to-be-tested, to achieve the effect of one-dimensional heat transfer. When the temperatures on both sides of the insulation material being tested come to a stable state, the temperatures, the thickness of the material, and the heat flux, are measured and used to calculate the heat conducting coefficient. The difference between the ideal two-dimensional heat transfer and the one-dimensional heat transfer is corrected by the results of a theoretical model.

This invention is a suitable for the measurement of k values of multi-layered compound material, for the use of controlling the heater by means of PWM (Pulse Width Modulation) of the digital electric circuit design so that a more stabilized temperature control may be achieved, and for measurement, control, calculation and display functions using a single-chip microcomputer.

DETAILED DESCRIPTION OF THE INVENTION

The insulation technique of the present invention may be applied with improved quality, manufacturing process, or structure of the insulating material. Whether it is the improvement in the quality of existing insulating material, or evaluating the on-site insulating effectiveness as the basis of improvement, the testing of the insulating effectiveness remains a necessity. For testing of insulating effectiveness on compound materials, especially the testing of a vacuum insulating layer or an on-site insulating layer, it is impossible to cut off the insulating layer and make them into test pieces to be placed into a traditional heat-flow gauge/insulation measuring apparatus for testing. The only apparatus which may be used for non-destructive insulating proficiency testing is a portable testing apparatus. However, all current portable insulating effectiveness measuring apparatuses use a transient mode for testing, and are merely suitable for testing on insulating layers with homogeneous material and unsuitable for testing on any compound materials.

As a result, this inventor has designed a portable and stabilized insulating effectiveness measurement apparatus, i.e. a "temperature measuring apparatus". It utilizes an electrically controlled heater installed at one side of the insulating material to form a constant high-temperature region, causing most of the heat transfer to concentrate in a longitudinal heat flux, which flows across the direction of the thickness of object-to-be-tested, to achieve the effect of one-dimensional heat transfer.

A type of insulating material's heat conductivity measuring apparatus, that is based on the theory of steady heat-transfer, is made up of two separated pieces which are pasted on the two sides of the object-to-be-tested during the application. One of the separated units heats up one side of the object-to-be-tested; with two heaters on one side of the insulating material to form a constant-temperature region through temperature control so that all of the heat from the heater near the object-to-be-tested flows through the object-to-be-tested. The other separated piece is equipped with a bottom testing plate. The maximum temperature is obtained based on the temperature distribution on the bottom. This temperature is equivalent to that when there is no lateral heat transfer in the object-to-be-tested. The heat conductivity is derived from the temperature difference on the two sides, and value of heat transferred, by the region's heater.

Figure 1:
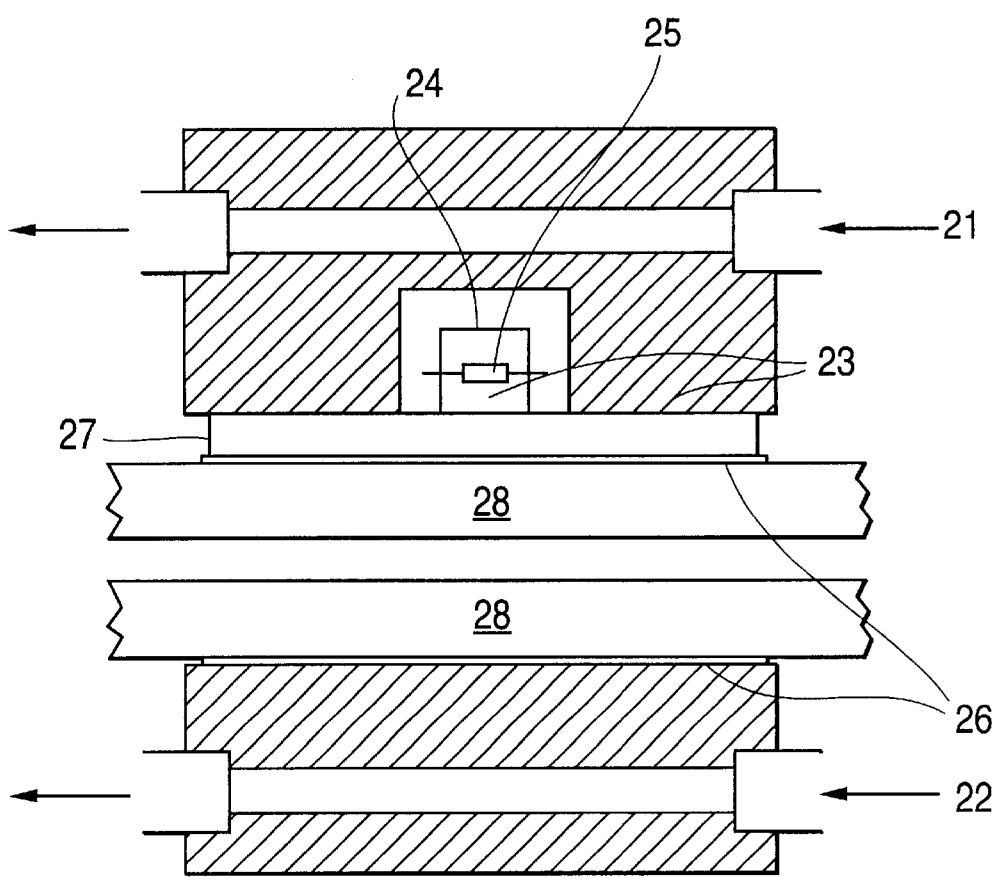
FIG. 1 is an illustration of conventional Collins insulation measuring apparatus.
Figure 2:
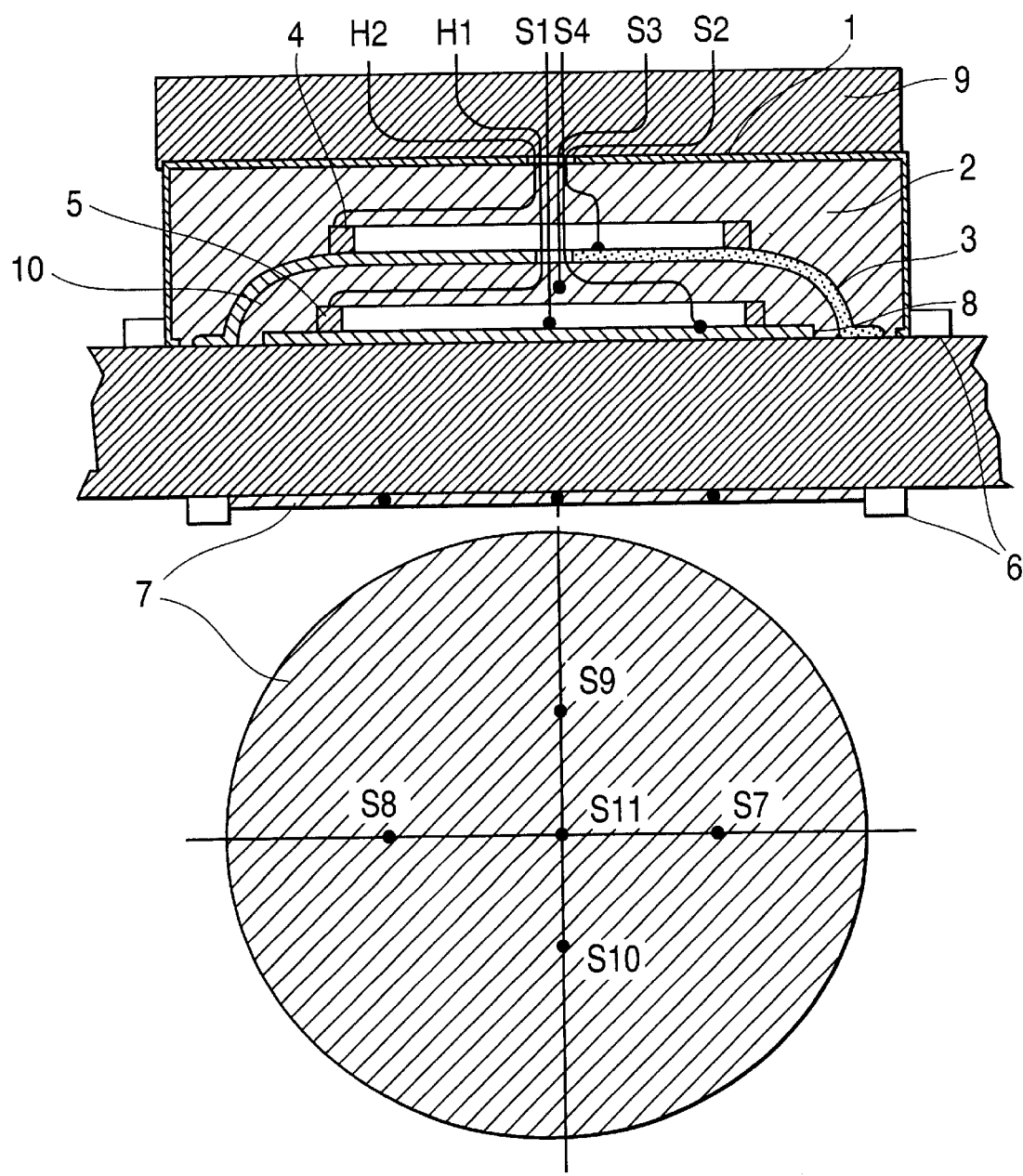
FIG. 2 illustrates a temperature measuring apparatus proposed in this invention.
Figure 3A:
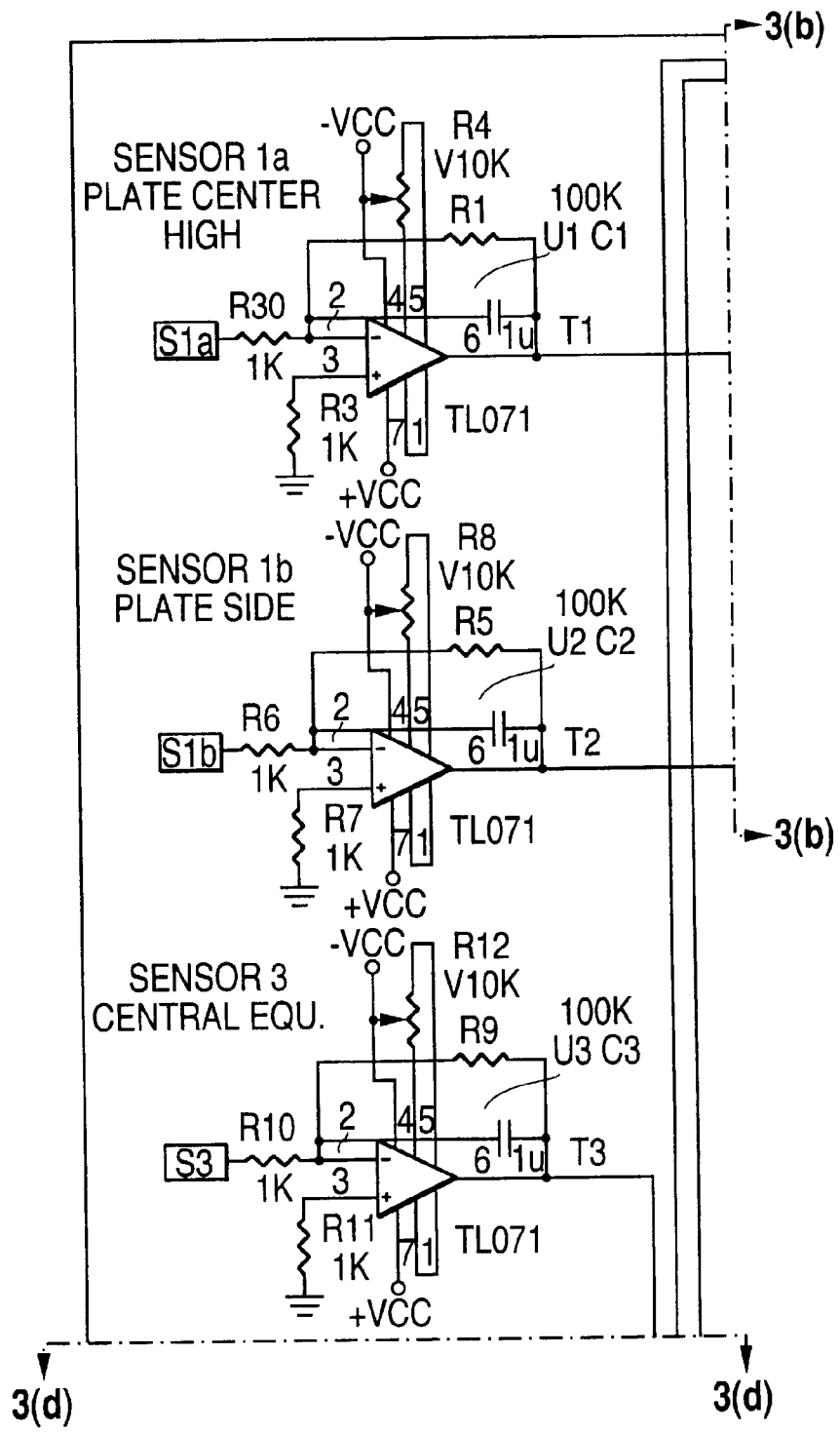
FIGS. 3(a)–3(f) illustrates a circuit diagram in accordance with the present invention.
Figure 3B:
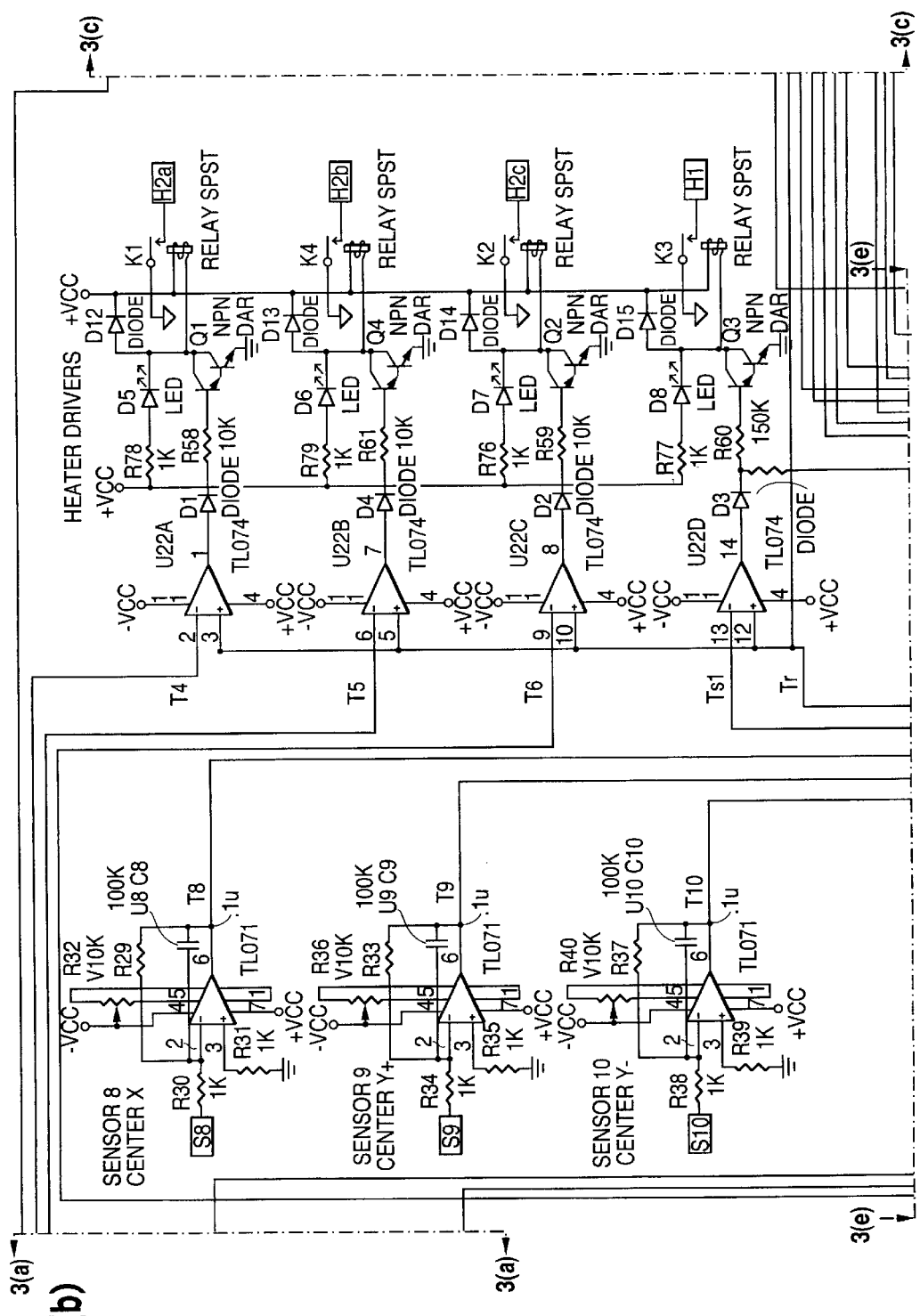
Figure 3C:
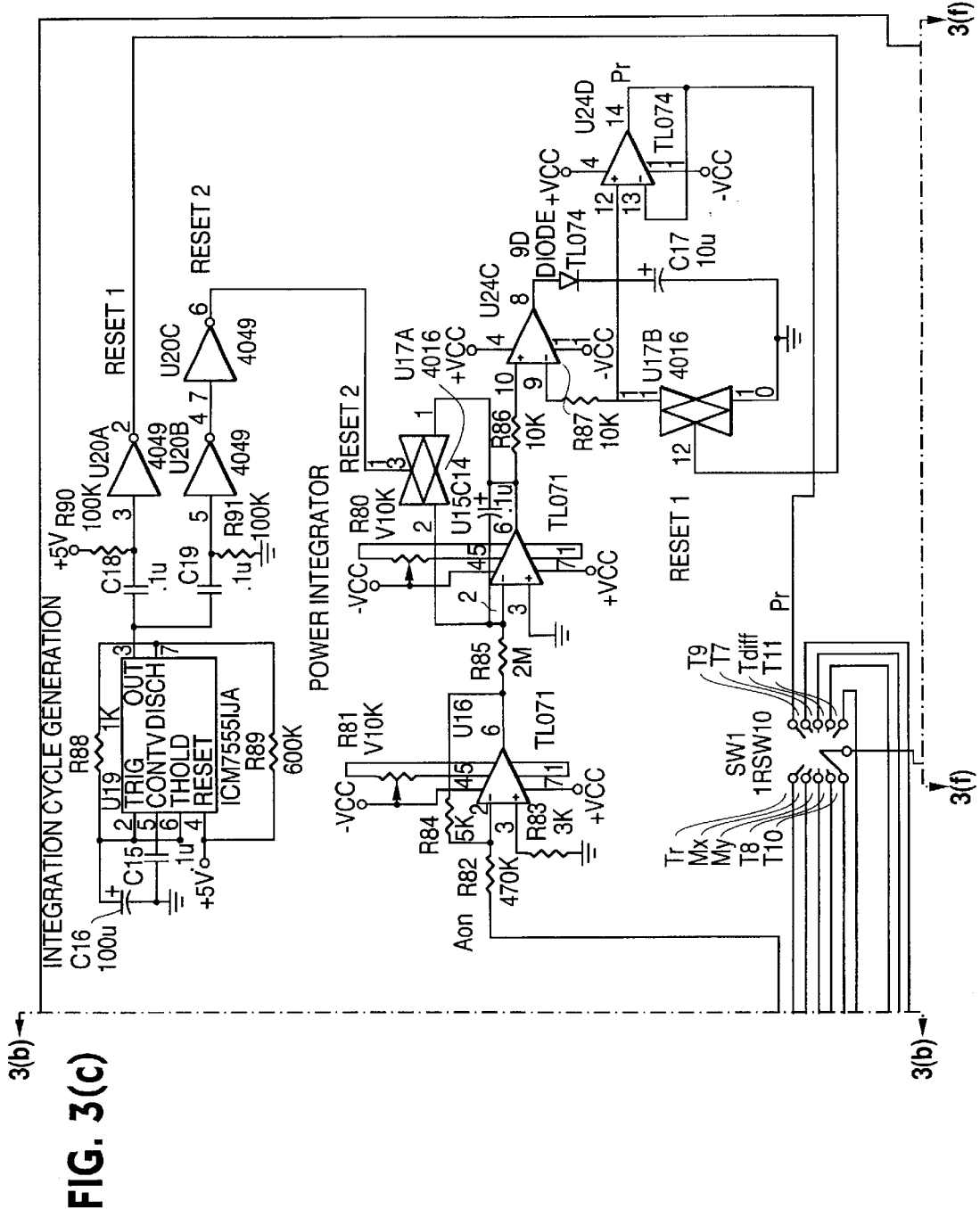
Figure 3D:
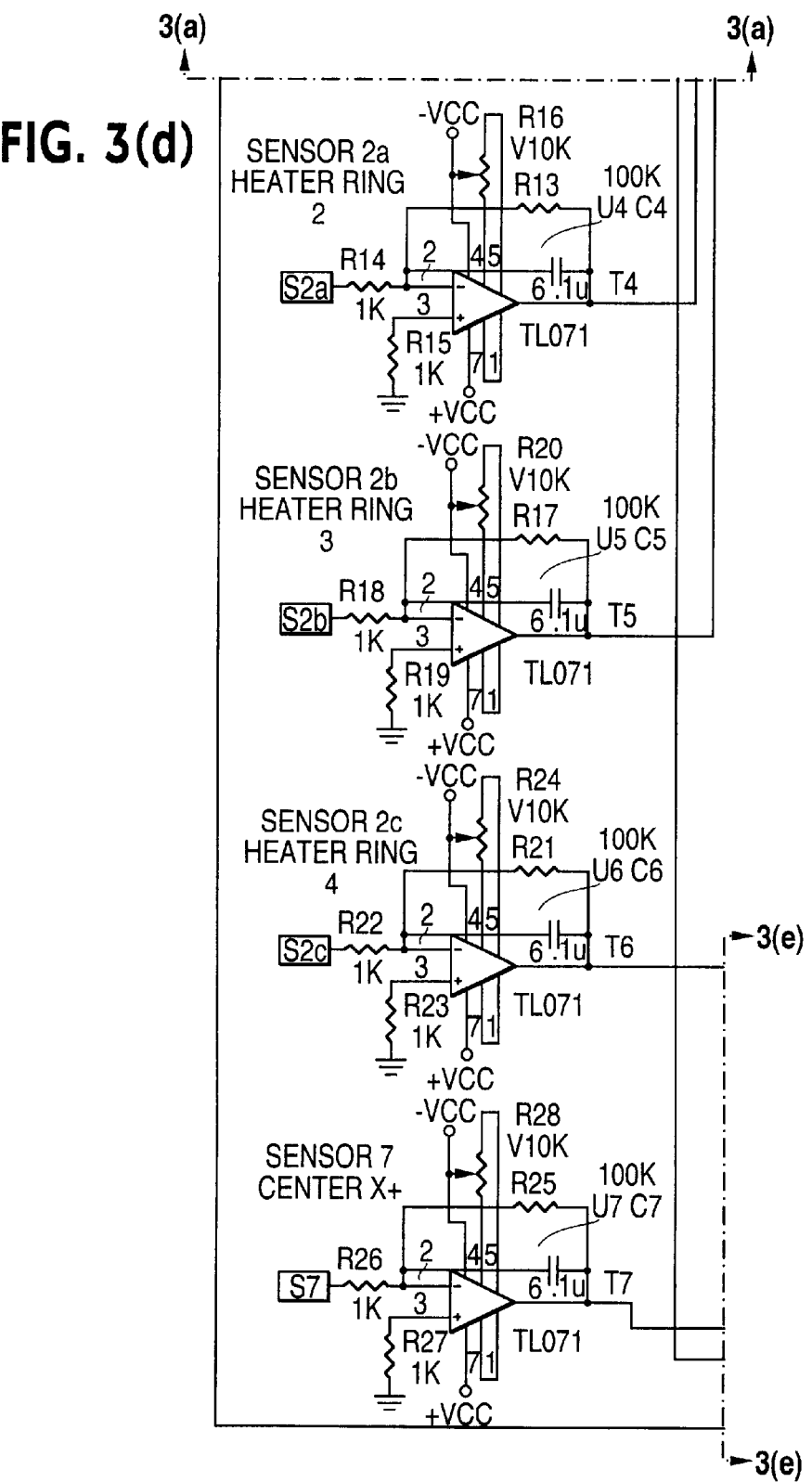
Figure 3E:
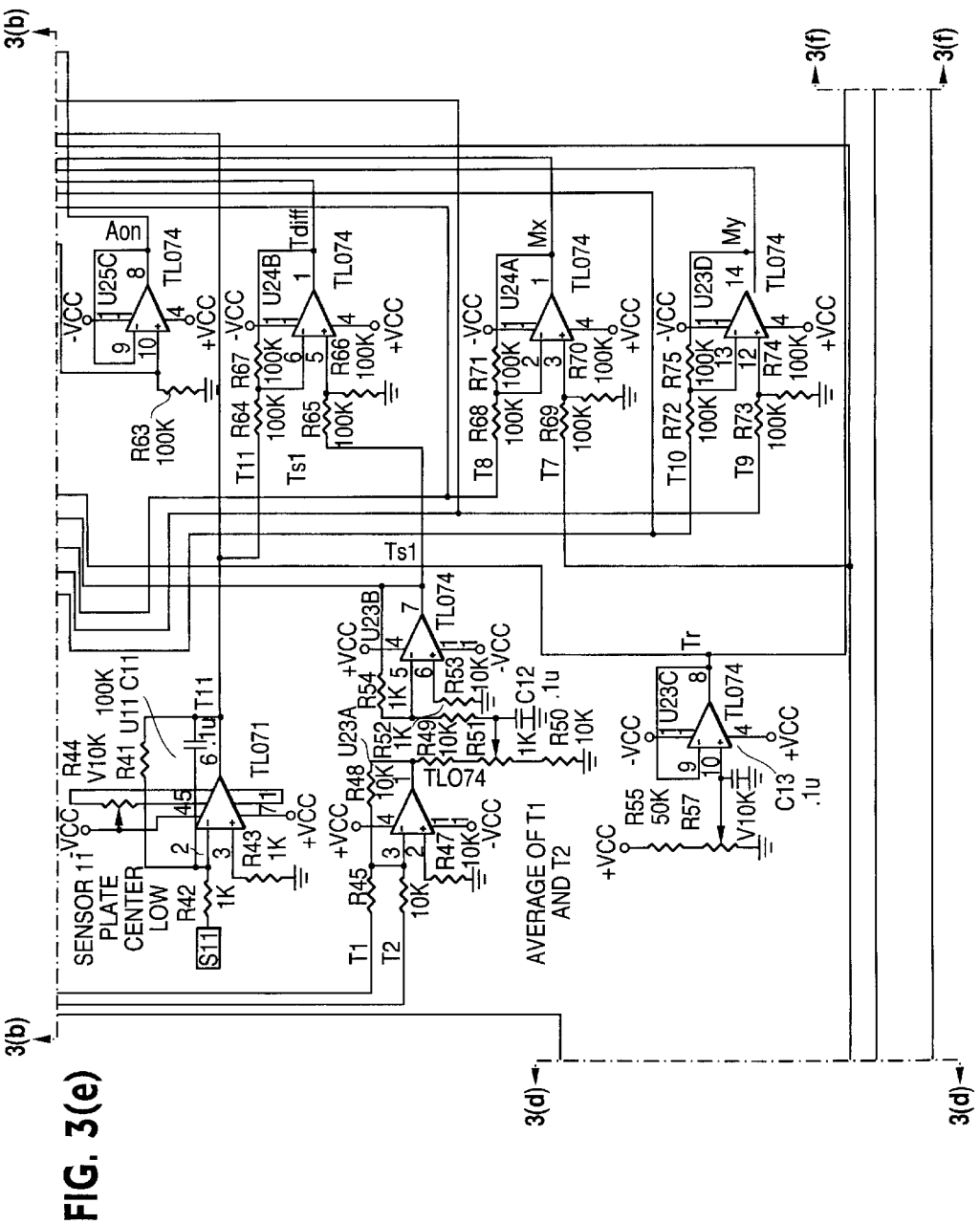
Figure 3F:
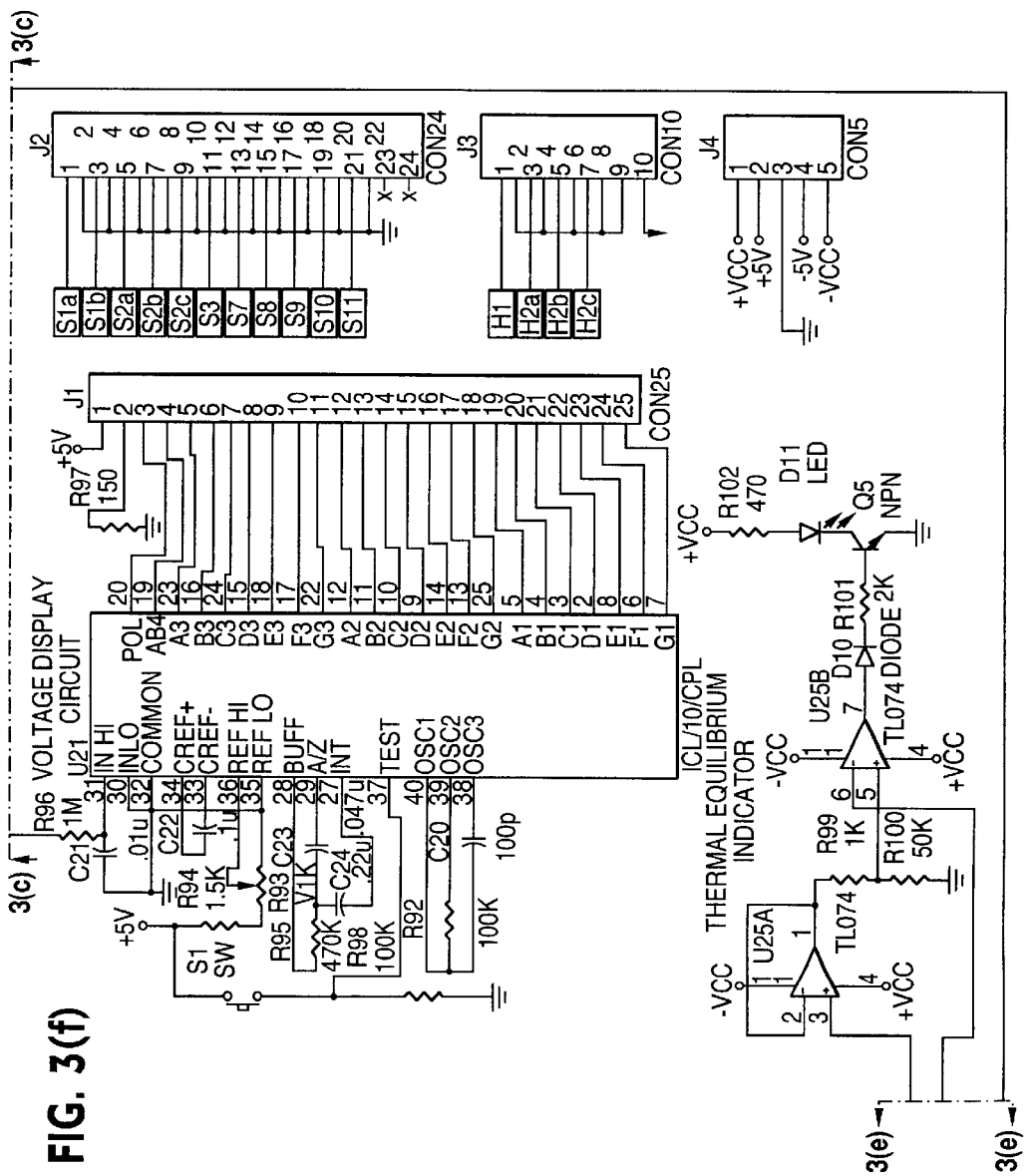
Figure 4:
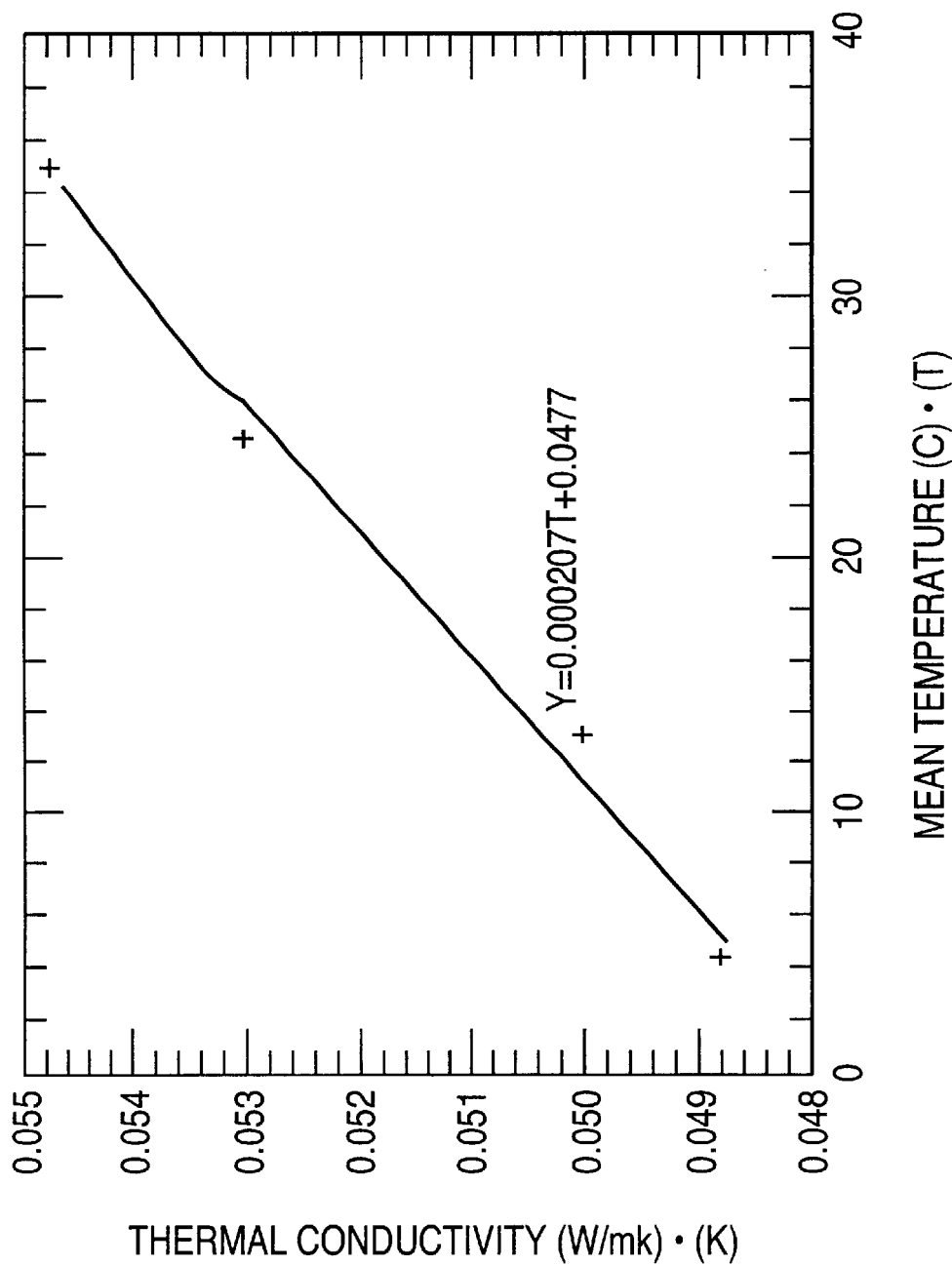
FIG. 4 illustrates the heat conducting coefficient according to the present invention.

The exterior of the temperature measuring apparatus proposed in this invention is the constant high-temperature region of the heating cap, as shown in FIG. 2, which includes insulating layer's shell (1), insulating layer (2), round cap (3), heater (4), heater (5), suction pad (6), bottom testing board (7), high-temperature round plate (8), controller and indicator (9), and constant-temperature region (10).

Temperature measuring apparatus's heater (5) is placed above the high-temperature round plate (8), and another heater (4) is placed above the round cap (3). Both the high-temperature round plate (8) and the round cap (3) are placed inside the shell (1) of the insulating layer. The center portion of the shell (1) is inserted with several signal controlling lines, which are S1, S2, S3, S4 respectively, and a suction pad (6) is attached to the bottom end on the side. There are five temperature measuring points, 57, 58, 59, S10 and S11 on top of the bottom measuring board (7), and a suction pad (6) is installed at the bottom portion on the side.

Temperature measuring apparatus's heater (5) is the source of heat which pass through the insulating material, while the heater (4) makes up a uniform temperature zone that forces heat from heater (5) to flow in the longitudinal direction. The high-temperature round plate (8) is made of material, such as copper, which has high conductivity so that the temperature in the high-temperature round plate will be uniform. A round cap (3) made of material, such as copper, which has high heat conductivity, is installed above the high-temperature round plate, and the heater (4) is placed on top of it to form a surface of homogeneous temperature. During testing, the heat flux is adjusted to be the same temperature as the testing surface. The few temperature control points are S1, S2, S3, and S4 separately; among which, S1 and S4 are responsible for monitoring the temperature on the high-temperature round plate (8), S2 is responsible for monitoring the temperature on the round cap (3), and S3 is responsible for monitoring the temperature for the constant-temperature region (10).

Material with low conductivity is placed between the round cap (3) and the high-temperature round plate (8) so that no significant temperature difference will occur. In order to avoid excessive heat required for the high-temperature round plate and the consideration for application safety, the insulation layer (2) above the round cap is also made with material of low conductivity. Both the insulating layer (2) and the constant temperature region (10) use silica particles as the material. The bottom testing board (7) is round, and there are five temperature measuring points (11) on top of it, including the right-side point (S7), the left-side point (S8), the upper point (11), the lower point (S10), and the center point (S11). The center point (S11) can be moved so that the temperature measured at the temperature measuring point (11) is at the maximum. As the lower testing board (7) is a round symmetrical object, its temperature is the same on the top and bottom, thus the center point (S11) does not appear to have any lateral heat conduction. In order to reduce any lateral heat conduction and for the temperature to reach a stabilized condition quickly, this lower test board (7) is made of teflon material which has low conductivity.

The usual one-dimensional heat transfer simulation must be carried out in a high-temperature region and low-temperature region using a circulating liquid to maintain a constant temperature. The temperature measuring apparatus proposed in this invention simplify the high-temperature and low-temperature regions in the common heat flow gauge/insulation measurement apparatus into an electrically heated high-temperature region and an atmospheric constant low-temperature region, as shown in FIG. 2. The geometric shapes are entirely round shapes in order to reduce the border effect, and simplify the heat transfer problem.

The differences between this invention and that of Collins' insulation measuring apparatus are as follows:

(1) This invention uses two electric heating units to form the inner and outer ring, and uses electric control to form a constant-temperature region; the structure is simple.

(2) There is no need to manufacture a constant-temperature region at the bottom. The corresponding point at the bottom of the center point on top is where the highest temperature is found, and it is theoretically the point of no lateral heat transfer. Simply put the electrically heated constant-temperature side on the object-to-be-tested, and the temperature distribution on the other side is taken, then calculate the heat conductivity for that material. As a result, prior electricity test is not required, and it can be used for testing the product directly.

(3) The forming of a constant-temperature region requires merely an electricity source, and it is highly-portable.

The design concept for a one-dimensional heat transfer simulation is to use a heating cap above the high-temperature heating plate to construct a high-temperature constant-temperature region so that all the heat generated from the high-temperature heating board will flow in the direction of the thickness of the insulating material. The circumferences of this heating cap will prevent horizontal heat transfer. As for the horizontal energy transfer in the insulating material, a heated region of a larger dimension and insulating material thickness ratio is used to reduce the error, and correction is done with theoretical calculation.

During the testing, firstly, set the temperature of the signal control S1 on the high-temperature round plate (8), and the temperature of the signal control S2 on the round cap (3). The heating tube H1 will heat up the heater (5) in order to raise the temperature of the high-temperature round plate (8). At the same time, the signal controls S1 and S4 detect the surrounding temperature condition. Meanwhile, the heating control H2 will heat up the heater (4) so that the temperature of the round cap (3) rises. When the signal control S3 detects that its temperature is coming near to the temperature of the high-temperature round plate (8), the heating stops immediately. This will maintain the temperature between the round cap (3) and the high-temperature round plate (8), and a constant-temperature region is thus obtained.

When measuring temperature at the lower testing board (7), only the center point (S11) on the lower testing board is used in the calculation of insulating effectiveness; while the right-side point (S7), the left-side point (S8), the upper point (S9), and the lower point (S10) are used to regulate the central position of the center point (S11) on the measuring plate. The absolute values of the right-left points (S7–S8) and the top-bottom points (S9–S10) must be controlled within a certain range to ensure the central position of the center point (S11). Control heaters (4) and (5) so that $T_{S1}=T_{S2}$, and obtain a constant temperature region (10) between the round cap (3) and the high-temperature round plate (8). The formula for calculating the heat conductivity is shown below:

Using the following formula and based on the five points on the bottom testing board, $$T(x,y)=ax^2+bx+cy^2+dy+e \qquad (1)$$

Derive five constant numbers a, b, c, d, e, and then through the condition where $$\frac{\partial T}{\partial x} = \frac{\partial T}{\partial y} = 0,$$

obtain the position $(x_{max}, y_{max})$ of the maximum temperature on the bottom testing board. Therefore, the maximum temperature on the bottom testing board is derived as follows, $$T_{max} = T(x_{max}, y_{max}) = e - \left(\frac{b^2}{4a} + \frac{d^2}{4c}\right) \qquad (2)$$

The heat transfer coefficient, k, is $$k = \frac{Q\Delta L}{A(T_{S1} - T_{max})}.$$

In particular, ΔL is the thickness of the object tested, and A is the area of the high-temperature round plate. Position of the lower board (7) can be adjusted so that S11 correspond to the point of Tmax.

As shown In FIG. 3 for the operation of the circuit diagram, the signal control may transmit the rising temperature level to the temperature control, and accomplish temperature control. In addition, the circuit portion may also indicate the efficiency calculation and the values. Therefore, the circuit portion includes temperature control, calculation, and values display.

Temperature control is achieved through the method of comparing circuits, i.e. comparing the temperature of the copper piece and the reference temperature to control the switch to the heaters. Calculation is done with accumulated scores of the signals when the heater is activated, within a certain time interval. The accumulated voltage is such that if all signals are at 1 with this interval of time, the final voltage value will be IV. The definition and operating methods for analog signal is elaborated below:

Reference temperature at the heated end:
Take the desired temperature and plot it into the thermal couple voltage and temperature formula, the voltage value obtained is $T_r$. Make adjustment by turning the adjusting knob on the reference temperature generator, and turn the selector to $T_r$ position, until the digital display indicates the value as $T_r$.

Signal Processing:
All voltage signals of the heat couplings are separated and amplified by the pre-amplifier. $T_{S1}$ represents the average temperature value between the signal control tubes S1 and S4, on the high-temperature end plate. S1 indicates the temperature measured by the signal control tube at the center point of the high-temperature end plate, while S4 indicates the temperature measured by the signal control tube at the circumference of the high-temperature end board.

After comparison of $T_{s1}$ and $T_r$, through the Comparator, the 0 and 1 signals obtained are Aon. When $T_{S1}<T_r$, then Aon is 1, causing the on/off switch to be in an on mode which then activates the heating tube H1 to heat up. The voltage value obtained by the signal control tube S2 will also be compared with $T_r$, and the result of the said comparison is to control the heater (4). And as described above, in order to regulate the forming of a constant-temperature region between the round cap (3) and the high-temperature round plate (8), heating of the heating H2 is controlled so that $T_{S1}=T_{S2}$. At this point, the voltage value obtained by the signal control S2 is compared with $T_r$ to control the heating of the heating H2. When signal control (S3) detects that the temperature of the constant-temperature region (10) reaches 98% of the $T_r$ value, the thermal equilibrium indicator light will be illuminated to indicate that the high-temperature round plate (8) has only downward heat transfer. The Q value, which is the heater's electric efficiency, utilizes the test value of certain voltage under the condition that Aon signal is 1 and within a certain period of time (it is 40 seconds for this system). The value obtained is a percentile value, times the efficiency of the heating H1 to obtain the total heat flux.

The temperature variation at the bottom of this temperature measuring apparatus is within 1° C., and corresponds to the center point of the heater. As a result of the symmetry, S11 is also the point of maximum temperature. Therefore, this invention utilizes a formula which uses the distribution of temperature, S7~11, from the five temperature measurements, S7~11, to obtain the maximum temperature $T_{max}$. When there is little temperature difference, $T_{max}$ obtained should possess a relatively higher accuracy.

This invention can be used to measure the heat conductivity of a simple or composite material. The insulation of most products in existence tend to be a composite structure, insulation material, or vacuum. The primary function of this invention is to measure all solid products, i.e. test the effective k value of the compound materials but not the individual k value of the component material. When Q is the heater's electric power, the k value for the compound material can be calculated by $$k = \frac{Q\Delta L}{A(T_{sl} - T_{max})}.$$

Although the K value of the insulating material will change with the temperature, such as when iron is at 0° C., k=35.8 Btu/hr, and when at it is at 100° C., it is 36.6 Btu/hr. However, the k value of insulation materials, such as PU foaming material, is relatively insensitive to temperature, thus, the heating region's temperature should be set during application. By using the same temperature to compare the insulation of different products, more consistent numerical values may be obtained.

This invention may be used to measure the k value of multi-layered compound materials. As it may be used to measure the insulating effectiveness of frozen/air-conditioned products, it is more acceptable to most enterprises, which is a main feature of this invention.

EXAMPLE

Use a 28 mm thick expanded polystyrene object for testing, the temperatures T1~T4 obtained from the signal control S1~S4 are shown in Table-1. The effective heat conductivity values obtained at different temperatures are 0.046, 0.065 W/m°C.

The same expanded polystyrene object is commissioned to the Energy & Resource Research Center for testing, and the heat conductivity obtained range from 0.048 to 0.055 W/m°C.

This invention utilizes the constant-temperature region surrounding the heater to cause heat to flow longitudinally, thus, theoretically, it is not affected by the A/ΔL ratio, and is suitable for testing the insulation thickness (~3 centimeters) used in freezing/air conditioning to obtain a good result.

TABLE 1

| Experiment | 1 | 2 |
|---|---|---|
| Heat Flux (Watt) | 3.70 | 2.08 |
| T1 (° C.) | 85.2 | 71.1 |
| T2 (° C.) | 85.6 | 71.8 |
| T3 (° C.) | 82.7 | 68.5 |
| T4 (° C.) | 86.1 | 72.3 |
| $T_{max}$ (° C.) | 28.9 | 26.6 |
| Derived k (w/m° C.) | 0.065 | 0.046 |

What is claimed is:

1. A temperature measuring apparatus, comprising:

a first heater unit;

a high-temperature round plate positioned below said first heater unit;

a round cap being positioned above said first heater unit;

a second heater unit positioned over said round cap;

a shell essentially surrounding, from at least three sides, said first and second heater units, said high-temperature round plate and said round cap; and a suction pad attached to a bottom of the temperature measuring apparatus, wherein said shell has a center portion for accommodating a plurality of signal control members for monitoring temperature, the plurality of signal control members operatively attached to physical locations of the temperature measuring apparatus.

2. The temperature measuring apparatus according to claim 1, wherein said high-temperature round plate is made of copper material.

3. The temperature measuring apparatus according to claim 1, wherein said round cap is made of copper material.

4. The temperature measuring apparatus according to claim 1, further comprising a test board attached to the bottom of the temperature measuring apparatus, said test board being made of TEFLON® material.

5. The temperature measuring apparatus according to claim 4, wherein said test board is round.

* * * * *